United States Patent [19]

Faughn

[11] Patent Number: 5,009,252

[45] Date of Patent: Apr. 23, 1991

[54] AIR DISTRIBUTION CONNECTOR VALVE

[75] Inventor: Jim A. Faughn, Bel Air, Md.

[73] Assignee: The United States of America as represented by the Secretary of the Army, Washington, D.C.

[21] Appl. No.: 519,518

[22] Filed: May 3, 1990

[51] Int. Cl.$^5$ .............................................. F16L 29/00
[52] U.S. Cl. .................................. 137/614.04; 285/91
[58] Field of Search ........................... 137/614, 614.04; 285/82, 91, 396

[56] References Cited

U.S. PATENT DOCUMENTS

| 3,028,179 | 4/1962 | Abramoska | 137/614.04 X |
| 3,191,972 | 6/1965 | Collar | 137/614.04 X |
| 3,478,302 | 11/1969 | Chirumbolo | 285/396 X |
| 3,625,251 | 12/1971 | Nelson | 137/614.04 |

Primary Examiner—John C. Fox
Attorney, Agent, or Firm—Saul Elbaum; Walter R. Baylor

[57] ABSTRACT

An air distribution connector valve mechanism includes a pair of mating connectors, each having a self-closing, one way valve arranged and adapted to interfere with the self-closing, one way valve of the other connector when the two connectors are coupled together, such that the two valves will then open for unrestricted passage of air therethrough. Each connector has a coupling mechanism for releasably coupling the two connectors together to cause the interference between them. Each of the valves includes a valve body, and a compression spring associated and aligned therewith, in a valve housing having an axis of symmetry within the associated connector. Each valve body is retained and slidable axially within the housing against the force exerted by the associated compression spring, the latter normally urging the valve body against an end wall of the housing to block an opening therein. The valve body has projecting spacers with passageways therebetween on its cylindrical surface for separation from the inner surface of the associated valve housing. Thus, air is allowed to pass from one end to the other of the coupled connectors by virtue of the respective valve bodies having been unseated from their associated end walls.

1 Claim, 2 Drawing Sheets

AIR DISTRIBUTION CONNECTOR VALVE

RIGHTS OF THE GOVERNMENT

The invention described herein may be manufactured, used, and licensed by or for the United States Government for governmental purposes without the payment to me of any royalty thereon.

BACKGROUND OF THE INVENTION

The present invention relates generally to air distribution systems, and more particularly to an air distribution connector valve for rapidly and positively connecting and disconnecting a life support system to and from a main supply of air.

Various life support systems have been proposed in the past to provide air flow or distribution to one or more human subjects under conditions in which a breathable atmosphere is otherwise unavailable. Exemplary of such conditions are heavy smoke encountered by fire fighters in burning buildings or during forest fires, exhaust fumes encountered by traffic observers in tunnels or other restricted areas, toxic gases which may be encountered by soldiers in the field of battle, or the loss of oxygen in a passenger aircraft in flight. Some life support systems comprise a breathing apparatus employing a filter to remove the noxious or toxic elements from the air. In general, however, most life support systems are characterized by a self-contained source or supply of breathable air, a mask or hood to be placed over the head or simply the eyes, nose, and mouth of the user, one or more hoses to convey the breathable air, and a valve system for turning on and shutting off the supply of air to the user under the user's control. In some instances, the system is intended for a single user, while in many others a single air supply is available for use by several persons.

In any event, prior art air distribution techniques in life support systems utilizing valving arrangements suffer certain disadvantages, principal among which are a lack of free flow of air through the open valve(s); difficulty of manually opening and closing the valve by the user, particularly in emergency situations; lack of a positive indication to the user that the valve is fully open or closed; and inadequate coupling mechanisms for the valves.

It is a principal object of the present invention to provide an improved life support system, and particularly to enhance the valve mechanism for air distribution in such a system.

SUMMARY OF THE INVENTION

The present invention is primarily intended to provide an improved mechanism by which members of a military tank crew, armored vehicle, command module or the like can quickly, efficiently and effectively couple and uncouple their life support systems, including air cooling vests and ventilated face piece masks to a main air distribution system used as a microclimate cooling system. The invention includes a positive locking connector which provides visual, audible, and tactile feedback when fully engaged, and a valve mechanism with little or no restriction to the air flowing through the connectors. The low restriction of air flow decreases demand on the air distribution system's ability to overcome the head loss, i.e., pressure restrictions, and thereby enables the use of a smaller system requiring less energy, size and space in vehicles, shelters and equipments in which such a microclimate cooling system must be employed to protect the occupants against a hostile environment.

According to a presently preferred embodiment of the invention, an air distribution connector valve comprises two mating components, each of which contains a self-closing one way valve, and which, when coupled together, open to allow air to pass with little or no restriction through the two valves. The valve couplers incorporate a one-quarter turn positive locking connector to facilitate the coupling and locking of the two halves. Such a configuration is particularly advantageous as an easy, effective and positive technique for use by soldiers to connect and disconnect their air umbilicals to a main air distribution system.

In particular, the preferred embodiment includes first and second mating connectors, each of which has a self-closing, one way valve arranged and adapted to interfere with the self-closing, one way valve of the other connector when the two connectors are mated together, whereby to open the two valves for unrestricted passage of air therethrough. Each connector also has an engagement mechanism for separably coupling the two connectors together to cause interference between the valves as noted above. Each of the valves includes a valve body, and a compression spring associated and aligned therewith, in a valve housing having an axis of symmetry within the associated connector. The valve body of each connector is retained and slidable axially within the valve housing against the force exerted by the associated compression spring, and the valve body is normally urged by the associated compression spring against an end wall of the housing having a circular opening, so that the valve body is normally seated against the end wall to block that opening. The valve body is cylindrical and includes spacers on its cylindrical surface for separating the valve body from the inner surface of the associated valve housing. The spacers are provided with holes to allow passage of air therethrough from the opening in the end wall to the other end of the associated valve housing when the valve body is unseated from the end wall.

Each valve body includes an end portion axially projecting through the opening in the end wall when the valve body is normally seated against the end wall of the associated valve housing. That end portion has an end surface arranged and adapted to confront and abut against the end surface of the valve body of the other connector and to interfere with one another as the two connectors are being coupled together, so that both valve bodies are unseated axially from the end wall of their associated valve housings when the two connectors are fully coupled together and are reseated when the two connectors are fully uncoupled, whereby an air distribution passageway is formed through the entirety of the coupled connectors and is automatically closed at each half of the uncoupled connectors.

The engagement mechanism of one connector includes a captive, rotatable ring having a plurality of spaced teeth on its inner surface, and the engagement mechanism of the other connector has a plurality of helical grooves equal in number to the number of teeth on the rotatable ring. The grooves are arranged and adapted to receive and accept the teeth, and, when accepted and the ring is rotated, the teeth ride within the grooves to fully couple or uncouple the connectors depending on the direction of the rotation of the ring.

The engagement mechanism with the helical grooves includes an over center pin for locking the teeth in position at the end of each of the associated grooves, the over center pin being overcome by exertion of pressure on the ring in the direction opposite that in which the teeth were fully engaged in the grooves.

The invention solves the problem of air line connections having a high air flow restriction, not having a positive coupling mechanism which couples and uncouples quickly with one hand. New solutions provided by the invention include the use of a Litton/Veam "CIR" type connector as the coupling mechanism and incorporating a one-way valving system in conjunction with it. The present invention has a number of advantages over prior art air distribution valve mechanisms, including low air restriction between coupling halves; positive one-quarter turn locking with visual, audible, and tactile feedback; reduced power/air flow demands on microclimate cooling systems; self-closing, one-way valves on both connector halves; ease of single handed operation; and ready decontamination owing to simplicity of construction.

BRIEF DESCRIPTION OF THE DRAWINGS

The above and still further objects, features, and attendant advantages of the invention will be better understood and appreciated from a consideration of the following detailed description of a presently preferred embodiment, taken in conjunction with the accompanying drawings in which.

DETAILED DESCRIPTION OF THE PREFERRED EMBODIMENT

Figure 1:
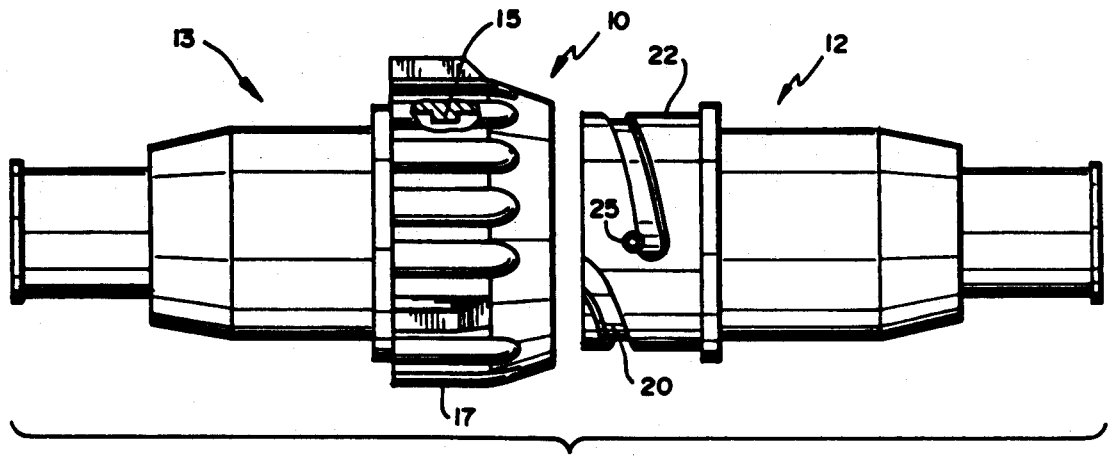
FIG. 1 is a side view of the male and female segments of a presently preferred embodiment of the invention, in uncoupled or valve closed configuration.
Figure 2:
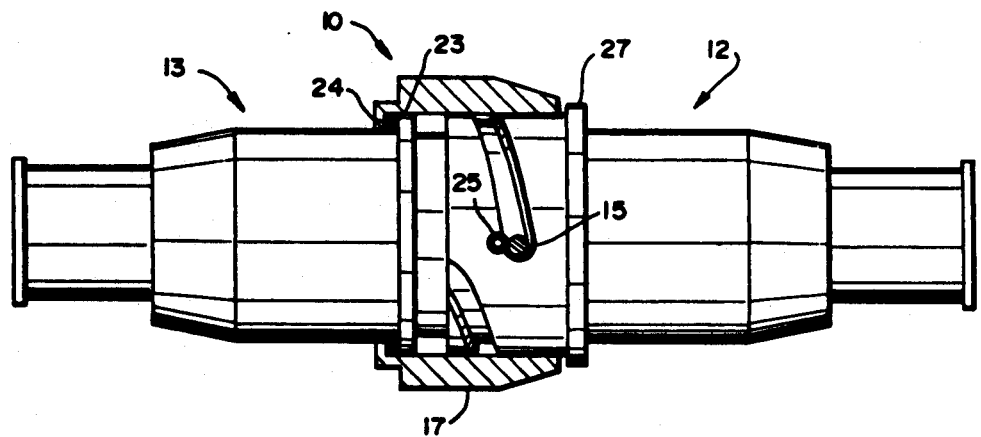
FIG. 2 is a side view, partly in section, showing the connector segments of FIG. 1 in coupled or valve opened configuration.
Figure 5:
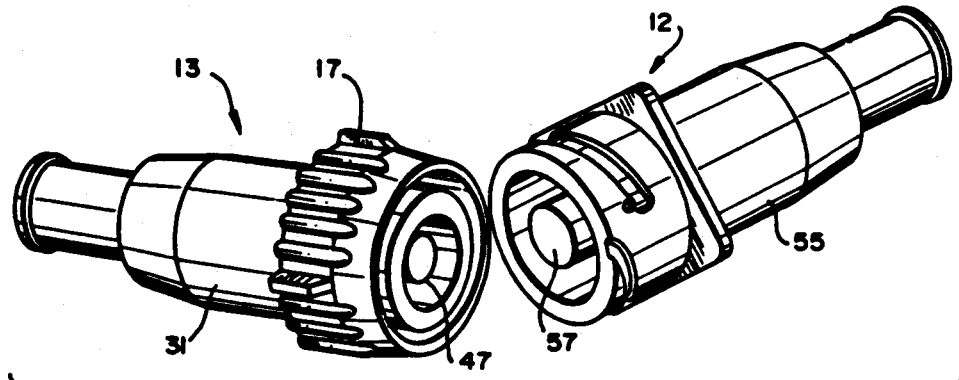
FIG. 5 is a perspective view of the two connector segments in the uncoupled state.

Referring now FIGS. 1, 2 and 5 of the drawings, a presently preferred embodiment of an air distribution connector valve 10 according to the invention includes first and second mating connectors 12, 13. Both the male connector 12 and the female connector 13 include a "CIR" Series coupling or engagement mechanism of a type widely used for electrical multipin connectors, manufactured by the Veam Division of Litton Systems, Inc. of Watertown, Connecticut. Such connectors are used in military, commercial, medical, geophysical, aerospace, ground support, and other applications, and feature a positive lock, quick-disconnect coupling and dynamic seal mechanism requiring only a quarter of a turn for full mating or release. Full coupling is indicated by audible, visual, and tactile sensing. High shock and vibration resistance to 50 g's are attained without the use of lockwires. The connector design avoids the use of coupling threads, which could gall or bind with wear or contamination. A stainless steel lock ring is provided at the high point of the bayonet ramp of the connector as a wear-free detent for extended coupling life. For a more comprehensive description of the CIR Series connector coupling mechanism, the reader is referred to descriptive literature for the connectors and to the connectors themselves, available from the Litton Veam Division.

For purposes of the present invention it is sufficient to note that the coupling mechanism of the connectors is configured as follows. Female connector 13 has three equally spaced lugs or teeth 15 disposed internally on and integral with a captive, rotatable ring 17. A portion of the female connector is shown in section in FIG. 1 to illustrate more clearly the location of one of the lugs 15 on the inner surface of ring 17. Male connector 12 has three equally spaced helical grooves 20 in a circumferential collar 22. The grooves 20 are arranged and adapted to receive and accept the lugs 15 of the female connector, so that after the connectors 12 and 13 are placed in confronting relationship and the end 22 of male connector 12 is inserted with proper alignment into the rotatable ring 17, the lugs are engaged in the grooves.

As shown in FIG. 2, the connectors 12 and 13 are fully coupled by rotating the ring 17 in a clockwise direction (as viewed from the left side of the Figure), thereby forcing the lugs 15 along the helical paths of grooves 20 until each of the lugs is positioned over center on a respective pin 25 near the end of the associated groove and finally resides seated against the end of the groove. The lugs are maintained in that position under the force of rearward axial tension placed on the lugs by a wave spring or wave washer 23 which is seated, together with an associated flat washer 24, between confronting flanges of ring 17 and the connector 13 body. In this manner, the male and female connector halves are maintained in positive locking connection, with the edge of ring 17 disposed in close proximity to a flange 27 of male connector 12. The user is thereby provided with visual, audible and tactile evidence that the two connectors are fully coupled together.

When the two connectors are to be separated (uncoupled), the user simply grasps the rotatable ring 17 with one hand, and exerts a force toward the male connector while twisting the ring in the counter-clockwise direction (as viewed in the same direction as before), to overcome the tension on locking pins 25 and return the lugs 15 along the grooves 20 to the exit points. Connector 13 is then merely pulled from connector 12 to fully uncouple the two. Thus, the connectors are readily coupled and uncoupled using only one hand. This assumes, of course, that one or both of the connector bodies are held to preclude rotation, but to allow sufficient axial movement for manual separation and recoupling.

Figure 3:
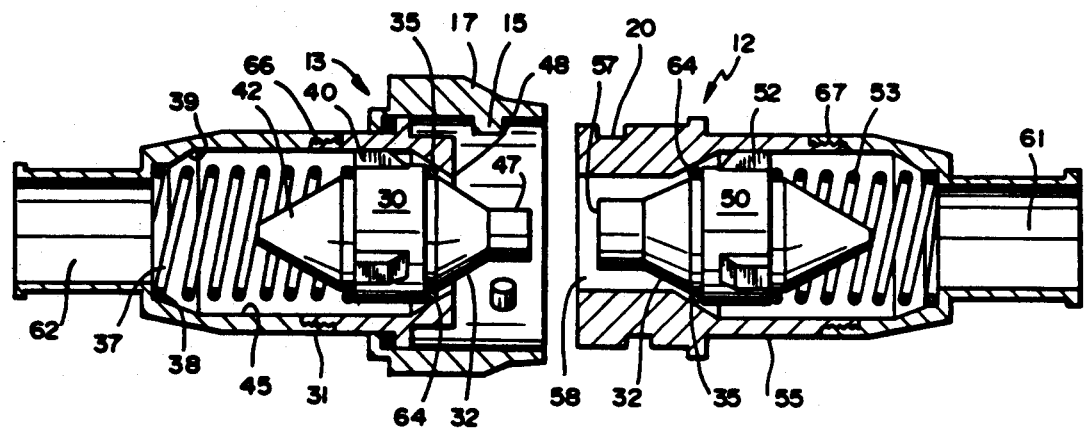
FIG. 3 is a side view corresponding to that of FIG. 1, in full section to show the internal components of the valving mechanism when the connectors are in the uncoupled configuration.
Figure 4:
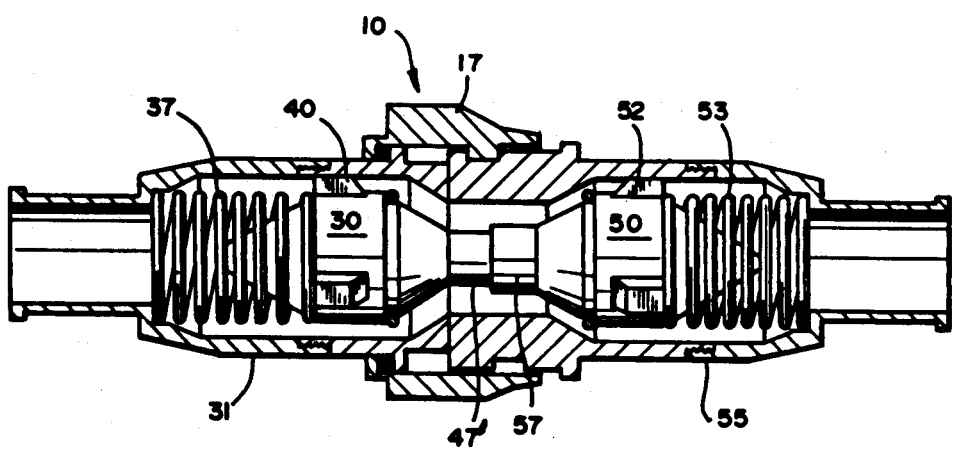
FIG. 4 is a section view of the internal components of the valving mechanism when the connectors are coupled as in FIG. 2.

Referring now to FIGS. 3 and 4, the presently preferred embodiment of the invention includes a sliding valve 30 having a substantially cylindrical body portion which is positioned along the axis of symmetry of housing 31 of female connector 13. Valve 30 is provided with an angled surface 32 which conforms to a similarly angled internal surface 35 of the end wall of housing 31. These two angled surfaces are urged toward one another and, but for the presence of a sealing O-ring 64 therebetween, would fully seat against each other. The O-ring is compressed under the force exerted by a compression spring 37. The compression spring is retained between a collar 38 of an opposite angled internal surface 39 of housing 31 and three spacers or lugs 40 equally spaced about the periphery of sliding valve 30.

A conical portion 42 of the surface of valve 30 resides within spring 37 in the assembly of the female connector. Spacers 40 serve to separate the valve 30 from the internal tubular surface 45 of housing 31 and to enable the valve to slide axially along that surface under oppositely directed forces exerted by or against the compression spring. It is important to note that the openings between the three separated spacers 40 provides three passageways between opposite ends of the valve body.

A cylindrical end portion 47 of sliding valve 30 normally projects through the circular opening 48 in the end wall of valve housing 31 when the angled surfaces of the valve and the end wall are urged together under the force exerted by the compression spring on the valve body. It will be observed from FIGS. 3 and 4 that a similar configuration of sliding valve 50, spacers 52, compression spring 53, and related internal surfaces of a housing 55, is provided within male connector 12. The cylindrical end portion 57 of valve 50 normally extends through a cylindrical hole 58 at the end wall of housing 55 under the influence of compression spring 53 on the valve. It will be understood, of course, that the two valve housings 31 and 55 are fabricated in any suitable manner to permit ease of assembly of the internal piece parts. For example, each of those housings may consist of two threaded mating halves which, when screwed together as at 66, 67, respectively, form a rigid housing body with a fluid-tight seal.

When the two connectors are brought together for coupling in the manner described above, the end portion 47 of sliding valve 30 and the end portion 57 of sliding valve 50 of respective connectors 13 and 12 abut against one another, causing interference between the two valves and forcing each to slide back against the force exerted by the associated compression spring. When the two connectors are fully coupled, a virtually unrestricted passageway exists between the opening 61 of connector 12 and the opening 62 of connector 13, via the openings between the respective sets of separated spacers 52 and 40 and the end wall openings 58 and 48, as shown more clearly in FIG. 4. In practice, the openings 61 and 62 of the two connectors are coupled to hoses for the desired air distribution from a supply to the user.

When the two connectors are uncoupled, the resulting removal of force against the compression spring in each connector causes the latter to urge its associated valve back to its normal seated position against the respective end wall to automatically shut off the distribution of air through the connector valve. The O-rings 64 seated on respective cylindrical surfaces adjacent the angled surfaces of the two sliding valve bodies assure an effective seal against the passage of air when the valve is closed.

Although a presently preferred embodiment of the invention has been disclosed herein, it will be apparent to those of ordinary skill in the field to which the invention pertains that variations and modifications of the described embodiment may be made without departing from the true spirit and scope of the invention. For example, the invention may be utilized as a valving mechanism for gases, or more broadly, fluids, other than air. Accordingly, it is intended that the invention be limited only to the extent required by the appended claims and the pertinent rules of law.

What is claimed is:

1. An air distribution connector valve comprising: first and second mating connectors;
   each connector including a self-closing, one way valve arranged and adapted to interfere with the valve of the other connector when the two connectors are mated together, whereby to open the two valves for unrestricted passage of air therethrough;
   each connector includes engagement means for separably coupling the two connectors together to produce the interference between said valves;
   each valve includes a valve body, and a compression spring associated and aligned therewith;
   each connector further includes a valve housing having an axis of symmetry; the valve body of each connector being retained and slidable axially within the valve housing against the force exerted by the associated compression spring, and the valve body being normally urged by the associated compression spring against an end wall of the housing having a circular opening therein, so that the valve body is normally seated against the end wall to block said opening;
   said valve body is cylindrical and includes spacing means on its cylindrical surface for separating the valve body from the inner surface of the associated valve housing,
   said spacing means have holes therein to allow passage of air therethrough from the opening in said end wall to the other end of the associated valve housing when the valve body is unseated from said end wall;
   each said valve body includes an end portion axially projecting through said opening when the valve body is normally seated against the end wall of the associated valve housing, said end portion having an end surface arranged and adapted to confront and abut against the end surface of the valve body of the other connector and to interfere with one another as the two connectors are being coupled together, so that both valve bodies are unseated from the end wall of their associated valve housings when the two connectors are fully coupled together and are reseated when the two connectors are fully uncoupled, whereby an air distribution passageway is formed through the entirety of the coupled connectors and is automatically closed at each half of the uncoupled connectors;
   said engagement means of one of said connectors includes a captive, rotatable ring having a plurality of spaced teeth on the inner surface of said ring;
   said engagement means of the other connector includes a plurality of helical grooves equal in number to the number of said teeth, and arranged and adapted to receive and accept the teeth, and, when accepted and the ring is rotated, the teeth ride within the helical grooves to fully couple or uncouple the connectors depending on the direction of rotation of the ring;
   said engagement means of the other connector further includes pin means for locking the teeth in position at the end of each of the associated helical grooves, said teeth and said pin means being releasable by exertion of pressure on the ring in the direction opposite that in which the teeth were fully engaged in the helical grooves.

* * * * *